(12) United States Patent
Ahn et al.

(10) Patent No.: US 11,781,217 B2
(45) Date of Patent: Oct. 10, 2023

(54) TRANSIENT SENSOR USING MOLYBDENUM DISULFIDE AND METHOD OF MANUFACTURING THE SAME

(71) Applicant: INDUSTRY-ACADEMIC COOPERATION FOUNDATION, YONSEI UNIVERSITY, Seoul (KR)

(72) Inventors: Jong Hyun Ahn, Seoul (KR); Xiang Chen, Nanjing (CN); Yong Ju Park, Seoul (KR); Min Pyo Kang, Seoul (KR)

(73) Assignee: INDUSTRY-ACADEMIC COOPERATION FOUNDATION, YONSEI UNIVERSITY, Seoul (KR)

( * ) Notice: Subject to any disclaimer, the term of this patent is extended or adjusted under 35 U.S.C. 154(b) by 0 days.

(21) Appl. No.: 16/237,133

(22) Filed: Dec. 31, 2018

(65) Prior Publication Data

US 2020/0208261 A1    Jul. 2, 2020

(51) Int. Cl.
*C23C 16/40* (2006.01)
*C23C 16/458* (2006.01)
(Continued)

(52) U.S. Cl.
CPC ........ *C23C 16/403* (2013.01); *C23C 16/4586* (2013.01); *G01N 33/5091* (2013.01); *C23C 16/345* (2013.01); *C23C 16/402* (2013.01)

(58) Field of Classification Search
CPC ..... C23C 16/403; C23C 16/4586; A61B 5/00; G01N 27/447; G01N 33/50
See application file for complete search history.

(56) References Cited

U.S. PATENT DOCUMENTS

| | | | |
|---|---|---|---|
| 10,006,882 B2 | 6/2018 | Prasad et al. | |
| 2011/0230747 A1* | 9/2011 | Rogers | A61B 5/05 600/377 |
| 2017/0363616 A1 | 12/2017 | Iyer et al. | |

FOREIGN PATENT DOCUMENTS

| | | |
|---|---|---|
| KR | 10-1692061 B1 | 1/2017 |
| KR | 10-1736910 B1 | 5/2017 |

(Continued)

OTHER PUBLICATIONS

Chen et al., CVD-grown monolayer MoS2 in bioabsorbable electronics and biosensors, Apr. 2018, Nature Communications, vol. 9, pp. 1-12 (Year: 2018).*

(Continued)

*Primary Examiner* — Dah-Wei D. Yuan
*Assistant Examiner* — Andrew J Bowman
(74) *Attorney, Agent, or Firm* — Sughrue Mion, PLLC

(57) ABSTRACT

The present invention discloses a transient sensor using molybdenum disulfide and a method of manufacturing the same. According to one embodiment of the present invention, the transient sensor using molybdenum disulfide includes a water-soluble substrate; a water-soluble insulating layer deposited on the water-soluble substrate; an electrode layer formed of any one of molybdenum (Mo) and magnesium (Mg) and formed on the water-soluble insulating layer; and a channel layer formed of molybdenum disulfide and formed on the water-soluble insulating layer to be connected to the electrode layer. In addition, when the transient sensor is inserted into living matter, the transient sensor can be dissolved within a critical time in the living matter.

4 Claims, 24 Drawing Sheets

(51) Int. Cl.
  G01N 33/50  (2006.01)
  C23C 16/34  (2006.01)

(56)   References Cited

FOREIGN PATENT DOCUMENTS

KR   10-2017-0088003 A   8/2017
KR       10-1779264 B1   9/2017

OTHER PUBLICATIONS

Minhoon Park et al. "$MoS_2$-Based Tactile Sensor for Electronic Skin Applications." Advanced Materials, 2016, vol. 28, pp. 2556-2562.
Xiang Chen et al. "CVD-grown monolayer $MoS_2$ in bioabsorbable electronics and biosensors." Nature Communications, Apr. 2018, vol. 9, No. 1690, pp. 1-13.
Communication dated Dec. 15, 2020, Issued by the Korean Patent Office in counterpart Korean Application No. 10-2019-0008734.

* cited by examiner

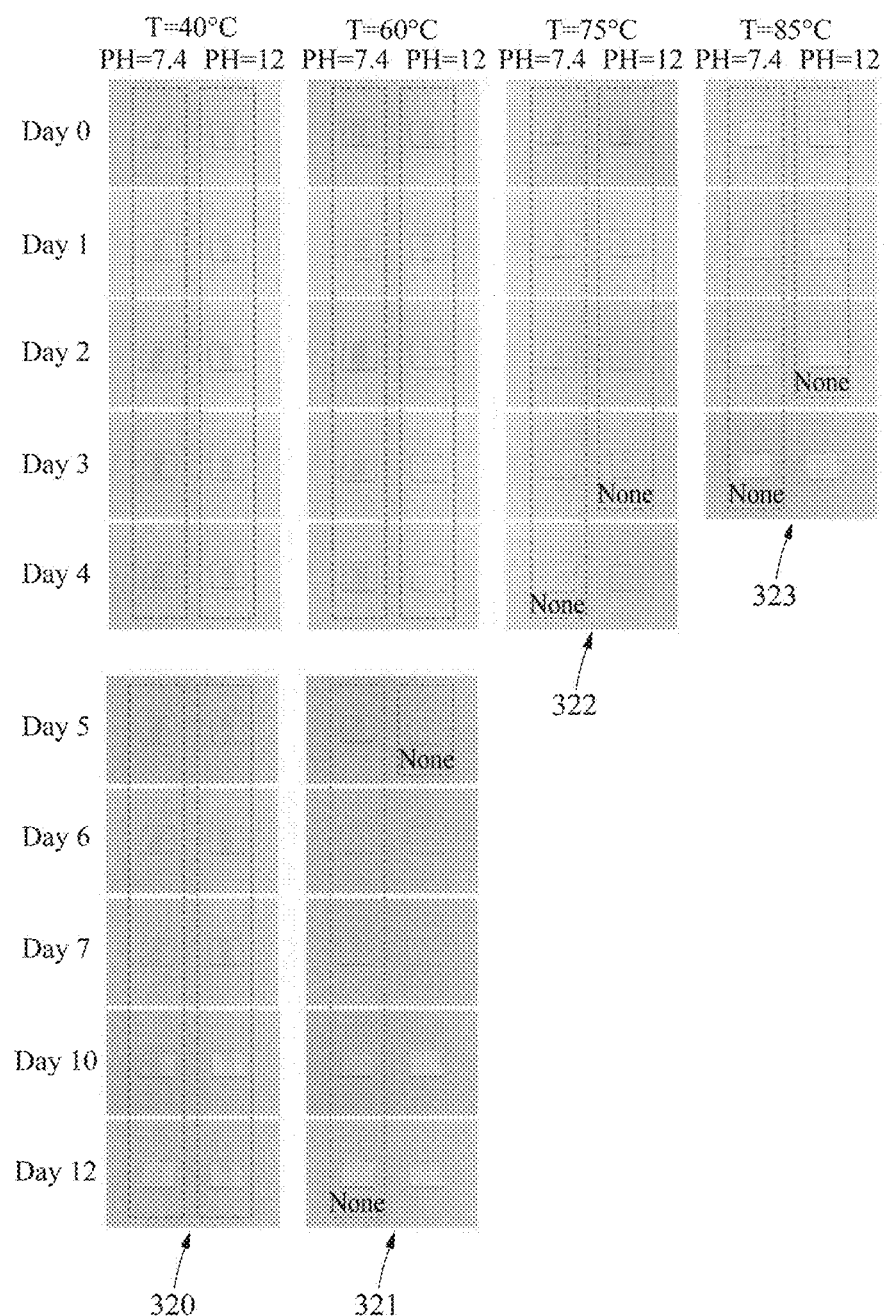

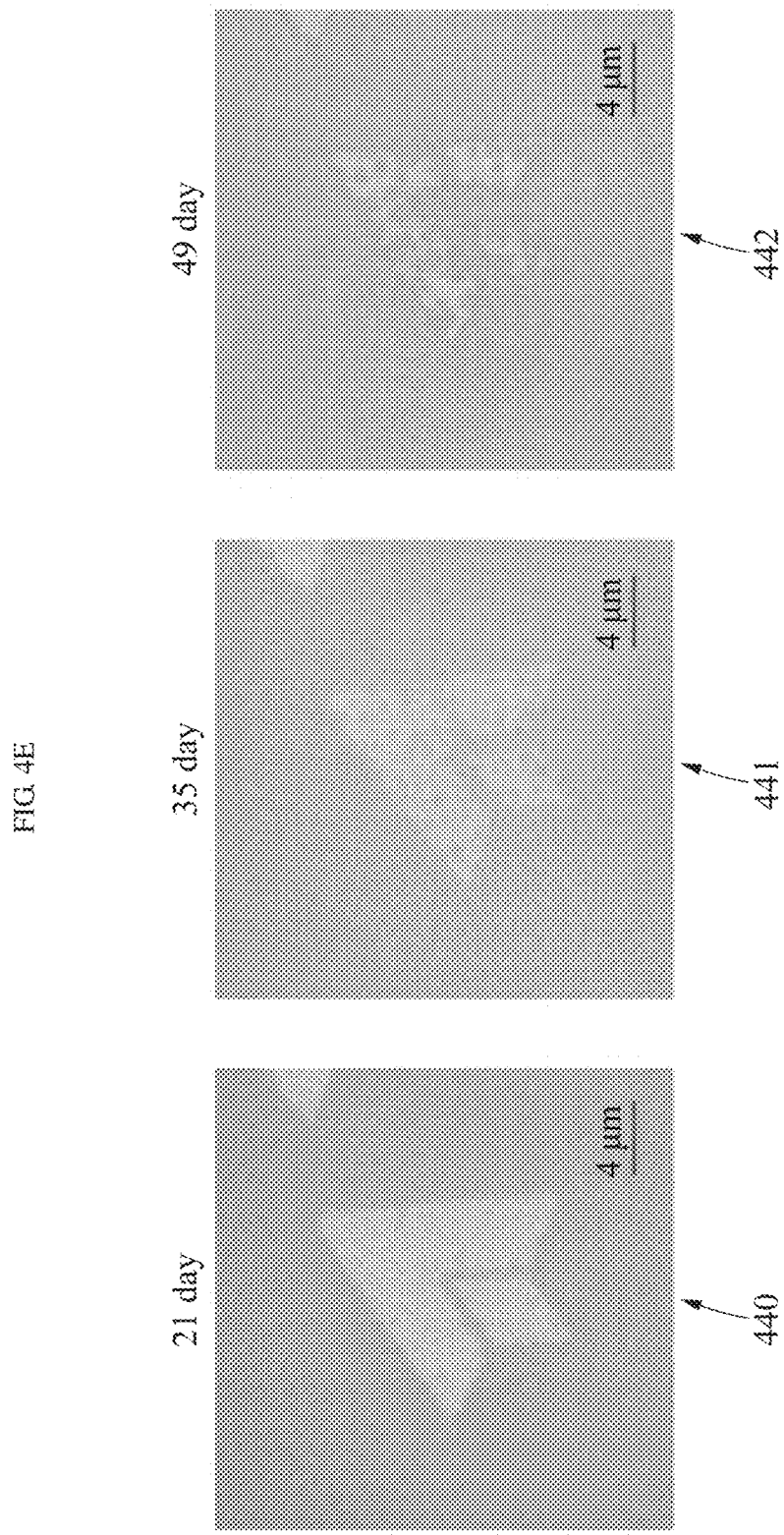

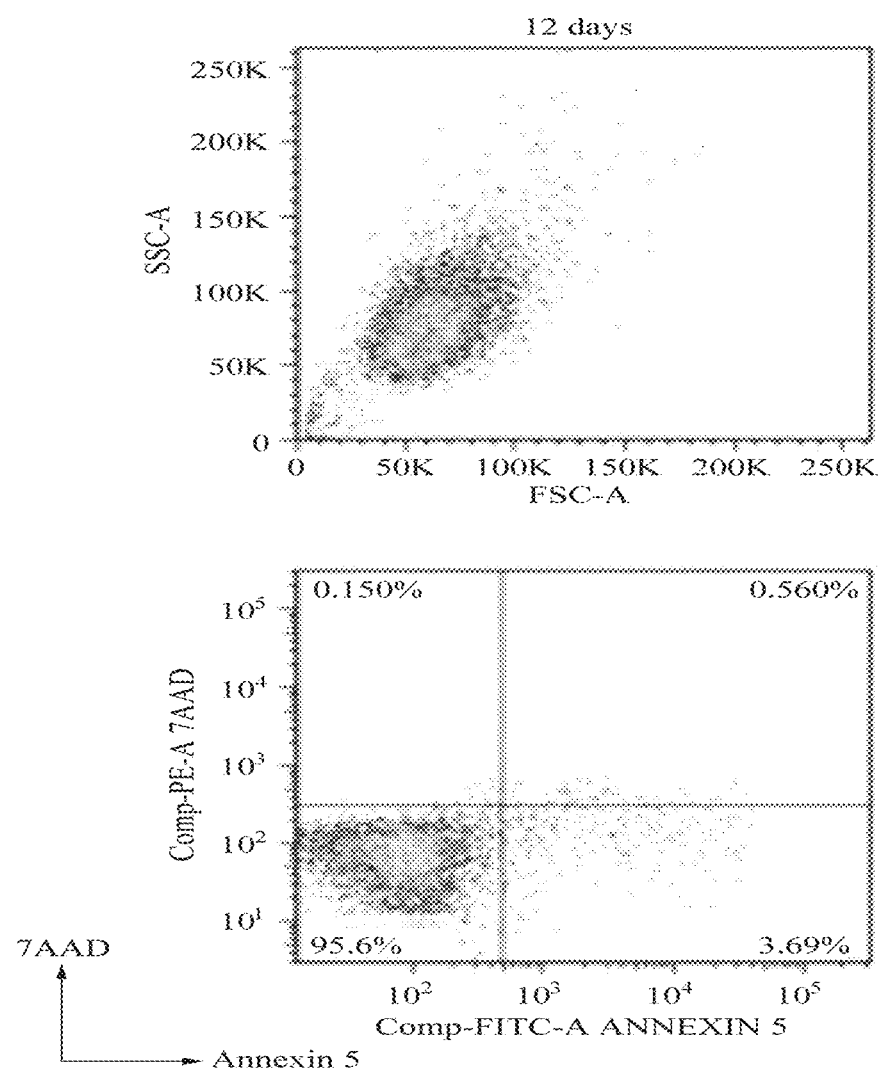

TRANSIENT SENSOR USING MOLYBDENUM DISULFIDE AND METHOD OF MANUFACTURING THE SAME

BACKGROUND OF THE DISCLOSURE

Field of the Disclosure

The present invention relates to a technical idea for manufacturing a transient sensor. More particularly, the present invention relates to a transient sensor using a two-dimensional material such as molybdenum disulfide ($MoS_2$), wherein the transient sensor is dissolved in a biological fluid such as blood, and a method of manufacturing the transient sensor.

Description of the Related Art

Recently, biological signal monitoring using biosensors has been actively studied worldwide.

Currently, the biosensor industry has a large market of about $5 billion globally. Among biosensors, biochips have high potential for development and can be applied to various fields, so the biochip industry is attracting attention as a future-oriented industry.

In addition, the market scale of biosensors is increasing by 10 to 15% every year. Therefore, economic value created by biosensor research can be very large.

Recently, development of a water-soluble silicon-based transient sensor and application thereof are expected.

The silicon-based transient sensor is manufactured to have a thin thickness and is attached to human body organs to measure biological signals. However, since the silicon-based transient sensor does not dissolve in the body, the sensor must be extracted after use.

To use biosensors in organs such as the heart and brain which are difficult to re-operate, new techniques are needed to overcome the above-described problems.

Unlike conventional materials such as silicon, when a two-dimensional material is used to manufacture a biosensor, the characteristics of the biosensor as a device can be obtained even when a single layer of the two-dimensional material is used. Therefore, two-dimensional materials can be used for manufacturing various sensors, e.g., ultra-thin film sensors.

Therefore, methods such as use of a two-dimensional material are required to solve the problems of a thin sensor manufactured according to conventional technology.

RELATED ART DOCUMENTS

Patent Documents

Korean Patent No. 10-1779264, "BIOLOGICAL INFORMATION MEASUREMENT DEVICE USING SENSOR ARRAY"

Korean Patent No. 10-1736910, "NONVOLATILE RESISTANCE MEMORY DEVICE MANUFACTURED USING BIOABSORBABLE AND BIODEGRADABLE MATERIAL"

Korean Patent No. 10-1692061, "FLEXIBLE AND TRANSPARENT MOLYBDENUM DISULFIDE-BASED GAS SENSOR AND METHOD OF MANUFACTURING THE SAME"

Non-Patent Document

Minhoon Park et al., "$MoS_2$-Based Tactile Sensor for Electronic Skin Applications", Adv. Mater. 2016, 28, 2556-2562

SUMMARY OF THE DISCLOSURE

Therefore, the present invention has been made in view of the above problems, and it is one object of the present invention to provide a transient sensor using molybdenum disulfide.

It is another object of the present invention to provide a transient sensor using a water-soluble electronic element insertable into the body, wherein the transient sensor is spontaneously dissolved after serving as a sensor.

According to the present invention, since the transient sensor using the electronic element is spontaneously dissolved in vivo, a process of re-incising the site where the transient sensor is inserted may be omitted, thereby reducing inconvenience of procedures and improving convenience of a subject.

In addition, procedural costs may be reduced by reducing procedural inconvenience.

It is another object of the present invention to provide a transient sensor that has excellent chemical stability and that can be manufactured to have a very thin thickness. According to the present invention, due to the chemical stability of the transient sensor, the transient sensor may not be easily transformed into other substances, and thus in vivo stability thereof may also be excellent. In addition, due to the thin thickness of the transient sensor, the dissolving time of the transient sensor in vivo may be remarkably reduced.

It is yet another object of the present invention to provide a method of manufacturing a transient sensor. According to the present invention, the method may improve economic efficiency in lab-on-a-chip and wearable electronic device fields and may contribute to leading research on bio-nano-materials.

In accordance with one aspect of the present invention, provided is a transient sensor using molybdenum disulfide including a water-soluble substrate; a water-soluble insulating layer deposited on the water-soluble substrate; an electrode layer formed of any one of molybdenum (Mo) and magnesium (Mg) and formed on the water-soluble insulating layer; and a channel layer including molybdenum disulfide in particle form formed on the water-soluble insulating layer to be connected to the electrode layer, wherein, when the transient sensor is inserted into living matter, the transient sensor is dissolved within a critical time in the living matter.

According to one embodiment of the present invention, the channel layer may be deposited as a single layer on the water-soluble insulating layer using metal-organic chemical vapor deposition (MOCVD) or may be deposited by performing electron beam deposition on the electrode layer. A channel may be deposited in a square wave form in the channel layer. The channel may be connected to the electrode layer.

According to one embodiment of the present invention, the channel layer may measure at least one of bioabsorbability, pressure, temperature, strain, and acceleration of the living matter.

According to one embodiment of the present invention, the critical time may be determined based on the particle size of the channel layer deposited using metal-organic chemical vapor deposition (MOCVD).

According to one embodiment of the present invention, the water-soluble substrate may be formed of any one of poly(lactic-co-glycolic acid) (PLGA) and polyvinyl alcohol (PVA).

According to one embodiment of the present invention, the water-soluble insulating layer may be formed of any one of an oxide layer and a water-soluble polymer complex by depositing any one of silicon oxide ($SiO_2$), silicon nitride ($Si_3N_4$), hafnium oxide ($HfO_2$), and magnesium oxide (MgO) and may be deposited on the water-soluble substrate using atmospheric pressure chemical vapor deposition (APCVD).

According to one embodiment of the present invention, at least one of the water-soluble substrate, the water-soluble insulating layer, the electrode layer, and the channel layer may be dissolved in bodily fluid contained in living matter.

According to one embodiment of the present invention, the channel layer may have a polycrystalline structure and may be deposited as a single-layer film on the water-soluble insulating layer.

According to one embodiment of the present invention, the biocompatibility of the channel layer may be determined based on the ratio of immune cells present in peripheral blood contained in the living matter into which the transient sensor is inserted and weight change of the living matter into which the transient sensor is inserted.

In accordance with another aspect of the present invention, provided is a method of manufacturing a transient sensor using molybdenum disulfide, the method including a step of depositing a water-soluble insulating layer on a water-soluble substrate; a step of forming an electrode layer using any one of molybdenum (Mo) and magnesium (Mg) on the water-soluble insulating layer; and a step of forming a channel layer including molybdenum disulfide in particle form on the water-soluble insulating layer to be connected to the electrode layer, wherein the transient sensor includes the water-soluble substrate, the water-soluble insulating layer, the electrode layer, and the channel layer, and, when the transient sensor is inserted into living matter, the transient sensor is dissolved within a critical time in the living matter.

According to one embodiment of the present invention, the step of forming a channel layer may include a step of determining the critical time by controlling the particle size of the channel layer deposited using metal-organic chemical vapor deposition (MOCVD).

According to one embodiment of the present invention, the method of manufacturing a transient sensor using molybdenum disulfide may further include a step of measuring at least one of bioabsorbability, pressure, temperature, strain, and acceleration of the living matter through the channel layer.

According to one embodiment of the present invention, the method of manufacturing a transient sensor using molybdenum disulfide may further include a step of determining the biocompatibility of the channel layer based on the ratio of immune cells present in peripheral blood contained in the living matter into which the transient sensor is inserted and weight change of the living matter into which the transient sensor is inserted.

According to the present invention, a transient sensor using molybdenum disulfide can be manufactured.

In addition, according to the present invention, a transient sensor that includes a water-soluble electronic element insertable into the body and that is spontaneously dissolved after serving as a sensor can be manufactured.

According to the present invention, since the transient sensor using the electronic element is spontaneously dissolved in vivo, a process of re-incising the site where the transient sensor is inserted can be omitted, thereby reducing inconvenience of procedures and improving convenience of a subject.

In addition, procedural costs can be reduced by reducing procedural inconvenience.

In addition, according to the present invention, a transient sensor that has excellent chemical stability and that can be manufactured to have a very thin thickness can be manufactured. According to the present invention, due to the chemical stability of the transient sensor, the transient sensor cannot be easily transformed into other substances, and thus in vivo stability thereof can also be excellent. In addition, due to the thin thickness of the transient sensor, the dissolving time of the transient sensor in vivo can be remarkably reduced In addition, the present invention can provide a method of manufacturing a transient sensor. According to the present invention, the method can improve economic efficiency in lab-on-a-chip and wearable electronic device fields and can contribute to leading research on bio-nanomaterials.

BRIEF DESCRIPTION OF THE DRAWINGS

FIGS. 3A to 3C include images and a graph for explaining the dissolution process of a transient sensor according to an embodiment of the present invention.

FIGS. 4A to 4E include images and graphs for explaining the energy properties of a transient sensor according to an embodiment of the present invention.

FIGS. 6A to 6E include graphs for explaining apoptosis related to a channel layer constituting a transient sensor according to an embodiment of the present invention.

DETAILED DESCRIPTION OF THE DISCLOSURE

Figure 1A:
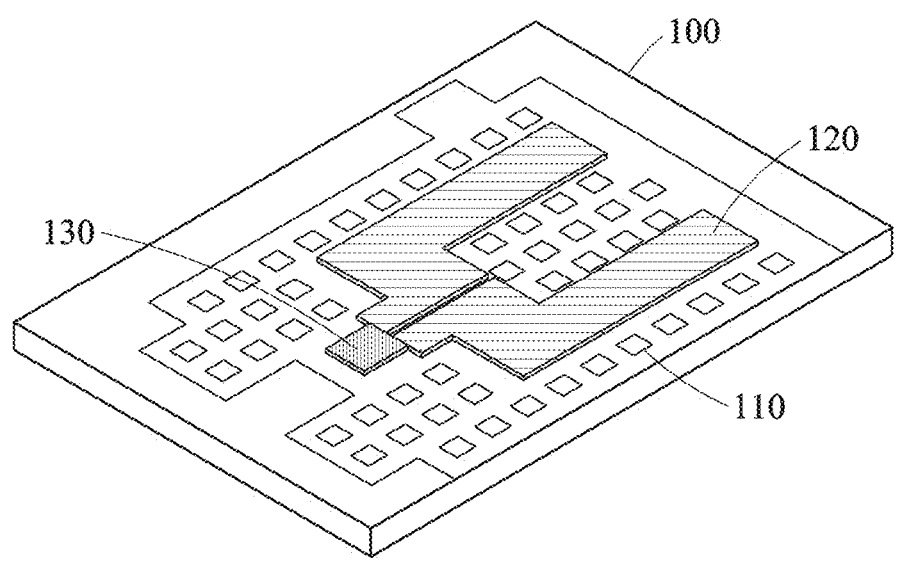
FIG. 1A is a drawing for explaining the structure of a transient sensor according to an embodiment of the present invention.

Hereinafter, embodiments of the present invention will be described with reference to the accompanying drawings.

It should be understood that the embodiments and terminology used herein are not intended to limit the techniques described herein to specific embodiments, but that various changes, equivalents, and/or alternatives of the embodiments may be included in the invention.

In the following description of the present invention, detailed description of known functions and configurations incorporated herein will be omitted when it may make the subject matter of the present invention unclear.

The terms used in the specification are defined in consideration of functions used in the present invention, and can be changed according to the intent or conventionally used methods of clients, operators, and users. Accordingly, definitions of the terms should be understood on the basis of the entire description of the present specification.

In the description of the drawings, like reference numerals may be used for similar elements.

The expression of singularity in the present specification includes the expression of plurality unless clearly specified otherwise in context.

As used herein, the expression "A or B", "A and/or B or at least one of A and B" and the like may include all possible combinations of listed items.

Terms such as "first" and "second" are used herein merely to describe a variety of constituent elements, but the constituent elements are not limited by the terms. The terms are used only for the purpose of distinguishing one constituent element from another constituent element.

It will be understood that when an element (e.g., first) is referred to as being "on", "connected to" or "coupled to" another element (e.g., second), it may be directly on, connected or coupled to the other element or an intervening element (e.g., third) may be present.

In this specification, the term "configured to" may be used interchangeably with the term "suitable for", "having ability to", "modified to", "made to", "capable of", or "designed to" depending on the situation.

In some circumstances, the expression "a device configured to" may mean that the device "can do" with other devices or components.

For example, in the phrase "process configured to perform A, B, and C", the processor may be a dedicated processor (e.g., embedded processor) for performing the operation, or a general-purpose processor (e.g., CPU or application processor) capable of performing corresponding operations by executing one or more software programs stored in the memory device.

In addition, the expression "or" means "inclusive or" rather than "exclusive or".

That is, unless otherwise mentioned or clearly inferred from context, the expression "x uses a or b" means any one of natural inclusive permutations.

FIG. 1A is a drawing for explaining the structure of a transient sensor according to an embodiment of the present invention.

Specifically, in FIG. 1A, each component included in the transient sensor is shown.

Referring to FIG. 1A, the transient sensor may include a water-soluble substrate 100, a water-soluble insulating layer 110, an electrode layer 120, and a channel layer 130.

According to one embodiment of the present invention, the water-soluble substrate 100 may be formed of any one of poly(lactic-co-glycolic acid) (PLGA) and polyvinyl alcohol (PVA).

For example, the water-soluble insulating layer 110 may be deposited on the water-soluble substrate 100 using chemical vapor deposition.

According to one embodiment of the present invention, the water-soluble insulating layer 110 may be formed of an oxide-based layer or a water-soluble polymer complex and may include a water-soluble protective layer.

In addition, the dissolving timing of the water-soluble insulating layer 110 may be controlled depending on the component content of any one of the oxide layer and the water-soluble polymer complex.

For example, the water-soluble insulating layer 110 may be formed of any one of an oxide layer and a water-soluble polymer complex by depositing any one of silicon oxide ($SiO_2$), silicon nitride ($Si_3N_4$), hafnium oxide ($HfO_2$), and magnesium oxide (MgO).

In addition, the water-soluble insulating layer 110 may be deposited on the water-soluble substrate 100 using atmospheric pressure chemical vapor deposition (APCVD).

According to one embodiment of the present invention, the electrode layer 120 may be formed of any one of molybdenum (Mo) and magnesium (Mg) and may be formed on the water-soluble insulating layer 110.

For example, the electrode layer 120 may receive biometric data through the channel layer 130.

According to one embodiment of the present invention, the channel layer 130 may be formed on the water-soluble insulating layer 110 to be connected to the electrode layer 120 and may include molybdenum disulfide in particle form.

For example, the channel layer 130 may be deposited as a single layer on the water-soluble insulating layer 110 using metal-organic chemical vapor deposition (MOCVD).

In addition, the channel layer 130 may be deposited by performing electron beam deposition on the electrode layer 120.

According to one embodiment of the present invention, the channel layer 130 may measure at least one of bioabsorbability, pressure, temperature, strain, and acceleration of the living matter.

For example, the channel layer 130 may have a polycrystalline structure and may be deposited as a single-layer film on the water-soluble insulating layer 110.

In addition, the water-soluble insulating layer 110 may be additionally formed on the electrode layer 120 and the channel layer 130 in the same pattern. Here, a structure in which the water-soluble insulating layer 110 is additionally laminated on the electrode layer 120 and the channel layer 130 will be described with reference to FIG. 2.

According to one embodiment of the present invention, when the transient sensor is inserted into the living matter, the transient sensor may be dissolved in the living matter within the critical time.

According to the present invention, since the transient sensor using the electronic element is spontaneously dissolved in vivo, a process of re-incising the site where the transient sensor is inserted may be omitted, thereby reducing inconvenience of procedures and improving convenience of a subject.

In addition, procedural costs may be reduced by reducing procedural inconvenience.

For example, the critical time may be determined based on the particle size of the channel layer deposited using metal-organic chemical vapor deposition.

According to one embodiment of the present invention, the transient sensor may include a two-dimensional material.

For example, in addition to molybdenum disulfide ($MoS_2$), the two-dimensional material may include tungsten sulfide ($WS_2$), molybdenum diselenide ($MoSe_2$), tungsten diselenide ($WSe_2$), molybdenum ditelluride ($MoTe_2$), and the like.

For example, to increase the lifespan of the transient sensor using a water-soluble electronic element, after completing manufacture of the sensor, the top layer of the transient sensor may be encapsulated using a polymer material.

According to the present invention, a transient sensor using a water-soluble electronic element insertable into the body may be manufactured. In this case, the transient sensor may be spontaneously dissolved after serving as a sensor.

Figure 1B:
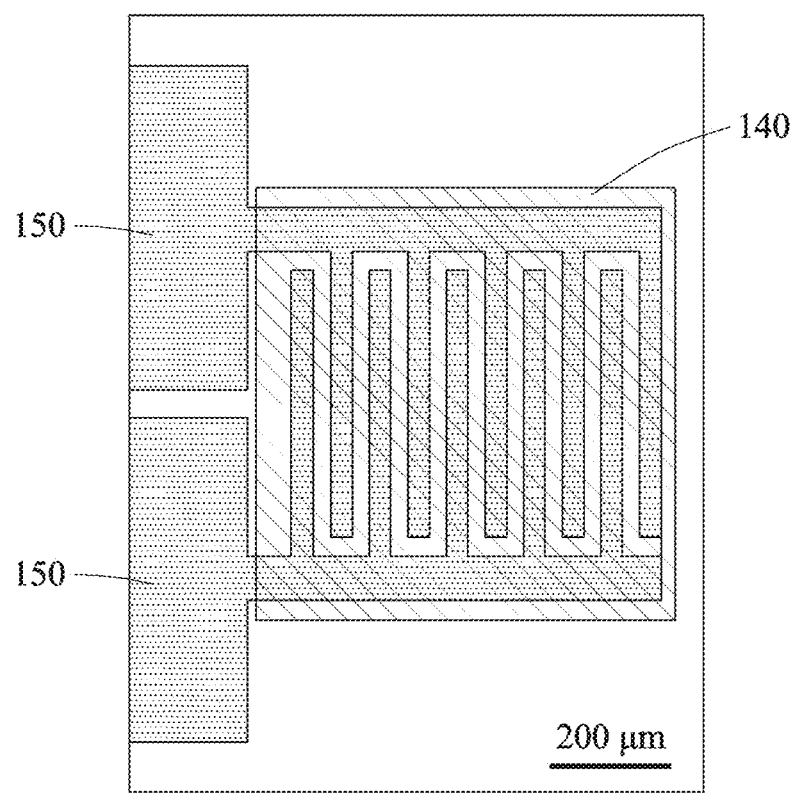
FIG. 1B is a drawing for explaining the channel layer of a transient sensor according to an embodiment of the present invention.

FIG. 1B is a drawing for explaining the channel layer of a transient sensor according to an embodiment of the present invention. Specifically, FIG. 1B illustrates the internal structure of the channel layer.

Referring to FIG. 1B, a channel layer 140 may be connected to an electrode layer 150.

According to one embodiment of the present invention, the channel layer 140 may be deposited by performing electron beam deposition on the electrode layer 150, and may include a channel.

For example, in the channel layer 140, a channel may be deposited in a square wave form, and the channel may be connected to the electrode layer 150. In this case, the channel may be deposited in a square wave form by being patterned in a square wave form.

According to one embodiment of the present invention, the channel layer 140 may collect data such as pressure, temperature, and strain of living matter through the channel.

For example, the channel of the channel layer 140 may be changed based on the particle size of the channel layer 140.

In addition, the channel layer 140 may be present as a face on the electrode layer 150.

Figure 2:
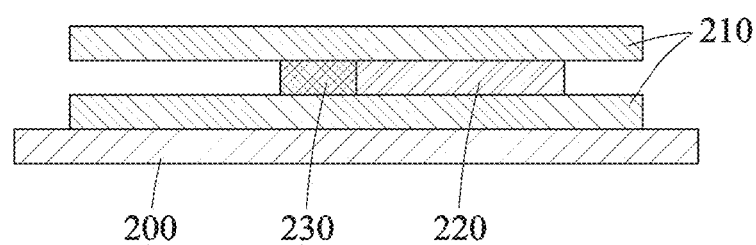
FIG. 2 is a drawing for explaining the laminated structure of a transient sensor according to an embodiment of the present invention.

FIG. 2 is a drawing for explaining the laminated structure of a transient sensor according to an embodiment of the present invention.

Referring to FIG. 2, the transient sensor includes a water-soluble substrate 200, water-soluble insulating layers 210, an electrode layer 220, and a channel layer 230.

According to one embodiment of the present invention, the water-soluble insulating layers 210 may be laminated on the water-soluble substrate 200.

For example, the water-soluble insulating layers 210 may be formed by laminating silicon dioxide ($SiO_2$) and may serve as a protective layer between the water-soluble substrate 200 and the electrode layer 220.

In addition, the water-soluble insulating layers 210 may be formed on the water-soluble substrate 200 by depositing an oxide such as silicon dioxide ($SiO_2$) using atmospheric pressure chemical vapor deposition.

For example, the electrode layer 220 may be laminated on the water-soluble insulating layers 210.

For example, the electrode layer 220 may be formed by depositing an oxide such as magnesium oxide (MgO).

According to one embodiment of the present invention, the channel layer 230 may be laminated on the water-soluble insulating layers 210 to be connected to the electrode layer 220.

According to one embodiment of the present invention, the channel layer 230 may be formed in a monolayer film structure.

For example, in the channel layer 230, a channel patterned in a square wave form may be formed.

According to one embodiment of the present invention, the water-soluble insulating layers 210 may be additionally laminated on the electrode layer 220 and the channel layer 230.

That is, the water-soluble insulating layers 210 may be present both above and below the electrode layer 220 and the channel layer 230.

Figure 3A:
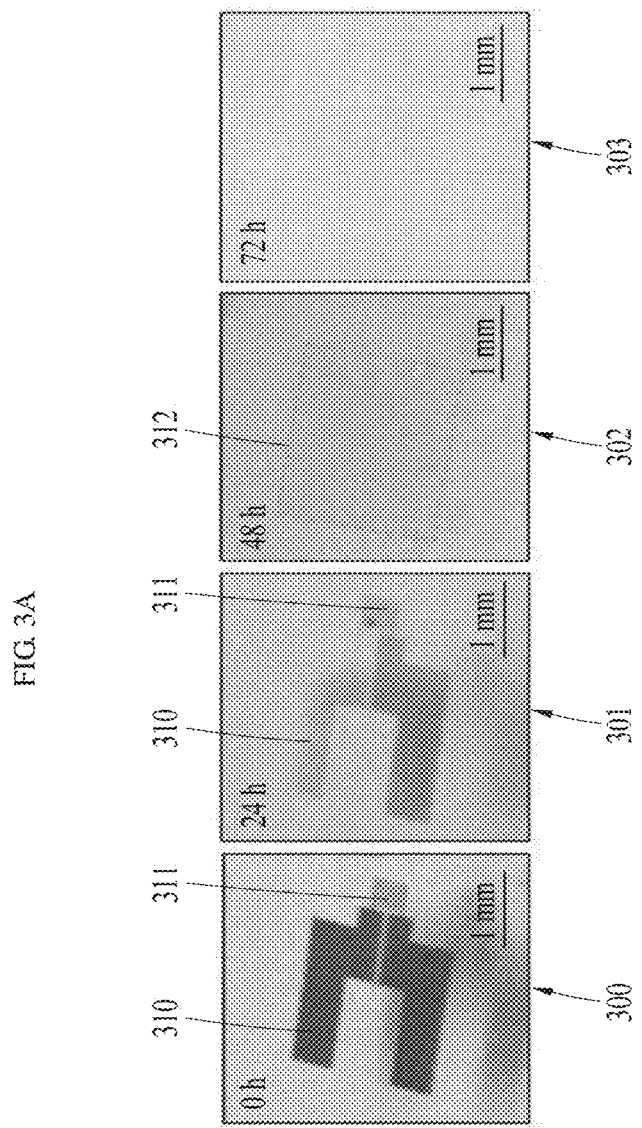
Figure 3C:
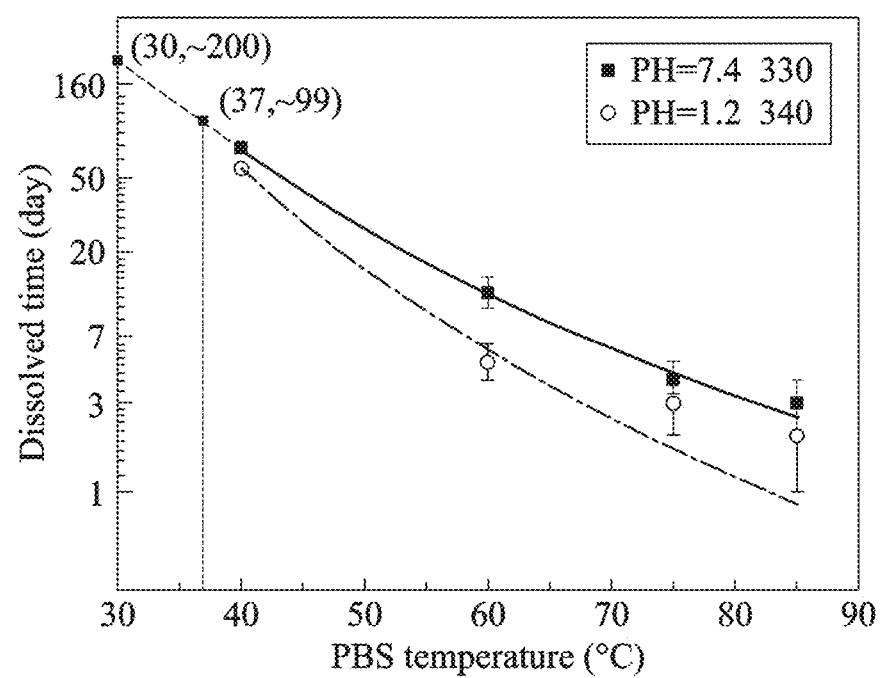

FIGS. 3A to 3C include images and a graph for explaining the dissolution process of a transient sensor according to an embodiment of the present invention.

FIG. 3A shows image 300, image 301, image 302 and image 303 of the transient sensor over time after the transient sensor is inserted into living matter.

Referring to image 300 of FIG. 3A, at the time when the transient sensor is inserted into the living matter, an electrode layer 310 and a channel layer 311 included in the transient sensor are intact.

Referring to image 301 of FIG. 3A, after 24 hours, parts of the electrode layer 310 and the channel layer 311 included in the transient sensor are dissolved by fluid present in the living matter.

Referring to image 302 of FIG. 3A, the electrode layer 310 and the channel layer 311 are dissolved and only a water-soluble insulating layer 312 remains. Referring to image 303 of FIG. 3A, the transient sensor inserted into the living matter is completely dissolved. For example, after about 72 hours, the transient sensor inserted into the living matter may be dissolved in fluid such as blood present in the living matter and may be dissolved.

FIG. 3B shows images 320 to 323 for explaining an experiment in which the transient sensor is immersed in a weakly basic liquid or a strongly basic liquid and the degree of dissolving of the transient sensor is checked at different temperatures.

Referring to images 320 to 323 of FIG. 3B, it can be seen that the transient sensor degrades faster under conditions of a strongly basic aqueous solution and high temperature.

That is, when the transient sensor is immersed in bodily fluid corresponding to a weakly basic liquid and incubated at a temperature of 40° C., the shape of the transient sensor is preserved for a certain period of time.

In addition, when culture temperature is increased, the transient sensor is more quickly dissolved.

FIG. 3C is a graph showing the dissolving time of the transient sensor depending on the acidity of a solution and culture temperature. Referring to FIG. 3C, when the transient sensor is immersed in a strongly basic aqueous solution and incubated at a high temperature, the transient sensor is more quickly dissolved. For example, the basic aqueous solution may include PBS (phosphate buffer saline).

In FIG. 3C, the horizontal axis of the graph corresponds to the temperature of a solution in which the transient sensor is immersed, and the vertical axis corresponds to the dissolving time of the transient sensor.

When dissolving time at a first pH 330 is compared with dissolving time at a second pH 340, dissolving time is shortened at a low pH (i.e., the second pH 340), and the dissolving time is shortened as the temperature of an aqueous solution increases.

FIGS. 4A to 4E include images and graphs for explaining the energy properties of a transient sensor according to an embodiment of the present invention.

Figure 4A:
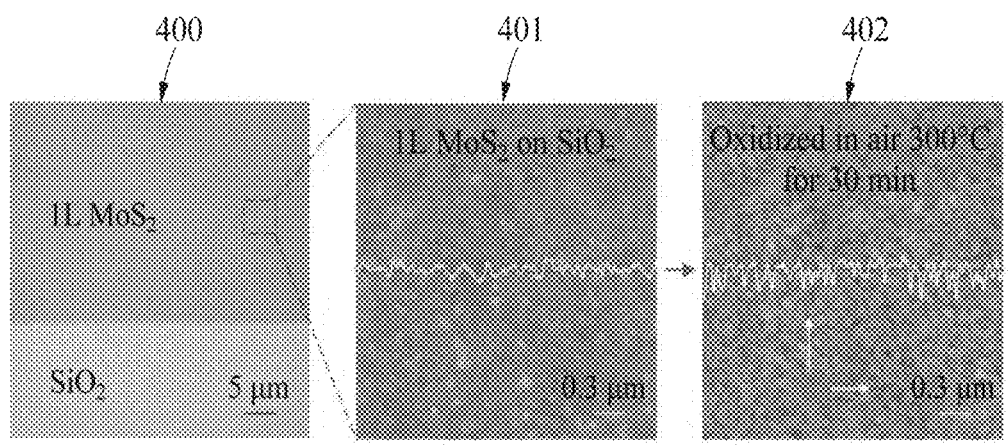

FIG. 4A includes images for explaining the optical properties of the channel layer formed on the insulating layer.

Image 400 of FIG. 4A shows a crystal structure of the channel layer deposited on the insulating layer using atmospheric pressure chemical vapor deposition.

Image 401 of FIG. 4A shows a crystal structure of the cross section of the channel layer. In addition, image 402 of FIG. 4A shows a particle boundary structure.

Figure 4B:
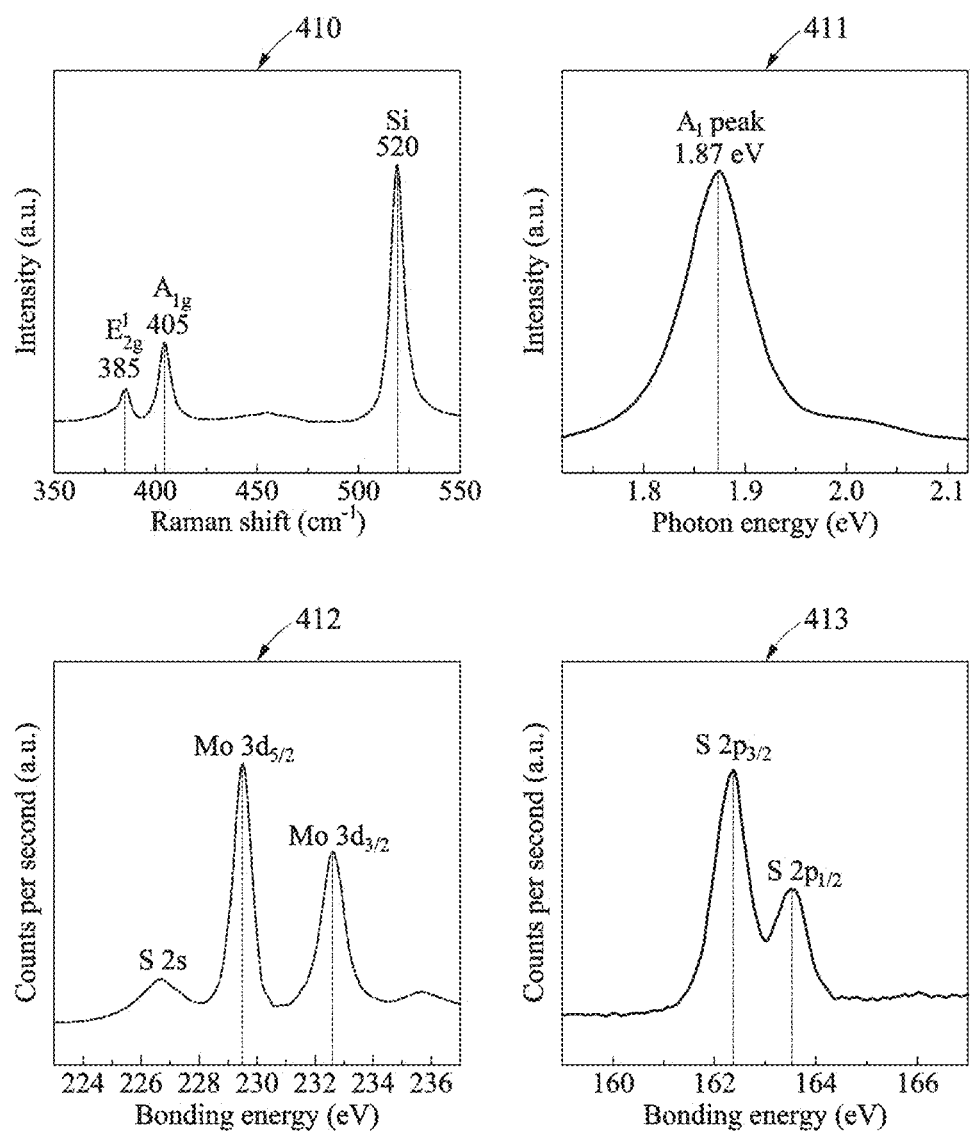

FIG. 4B includes graphs showing the energy properties of the channel layer deposited on the insulating layer using atmospheric pressure chemical vapor deposition.

In FIG. 4B, graph 410 shows intensity change depending on Raman shift, graph 411 shows intensity change depending on photon energy, and graphs 412 and 413 show change in counts per second depending on bonding energy.

Figure 4C:
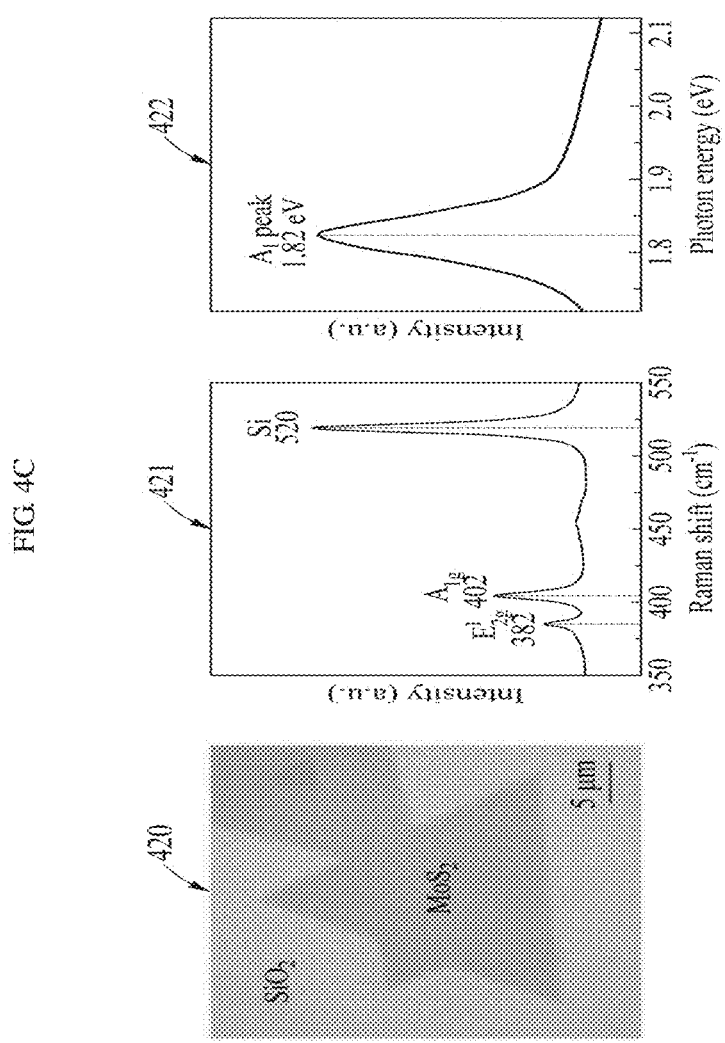

FIG. 4C includes an optical image 420 of the crystal structure of the channel layer deposited on the insulating layer using atmospheric pressure chemical vapor deposition and includes graphs showing Raman shift 421 and photon energy spectrum 422, respectively.

Figure 4D:
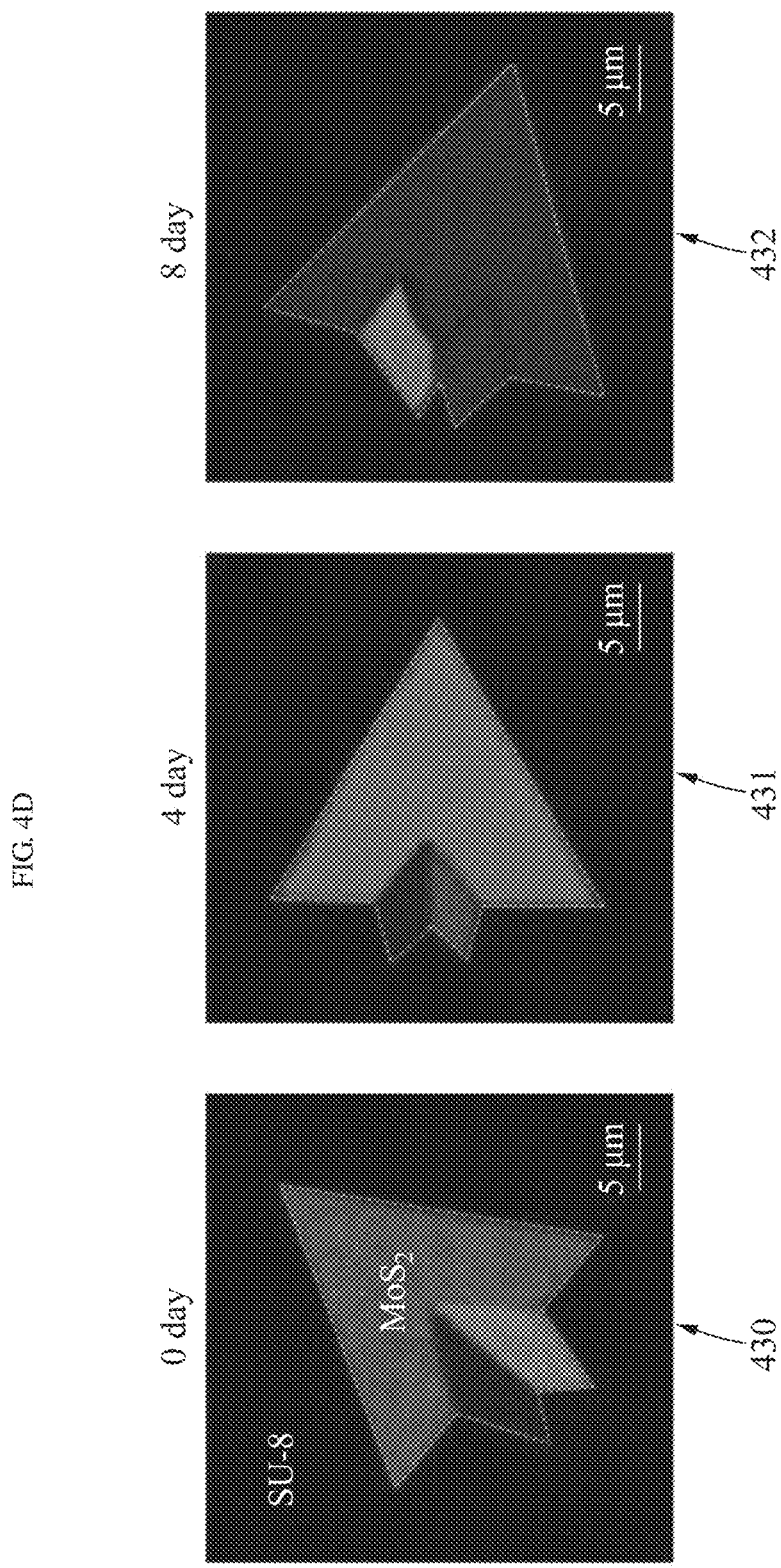

FIG. 4D and FIG. 4E illustrate a process in which the crystal structure of the channel layer deposited on SU-8 varies with time.

Figure 5A:
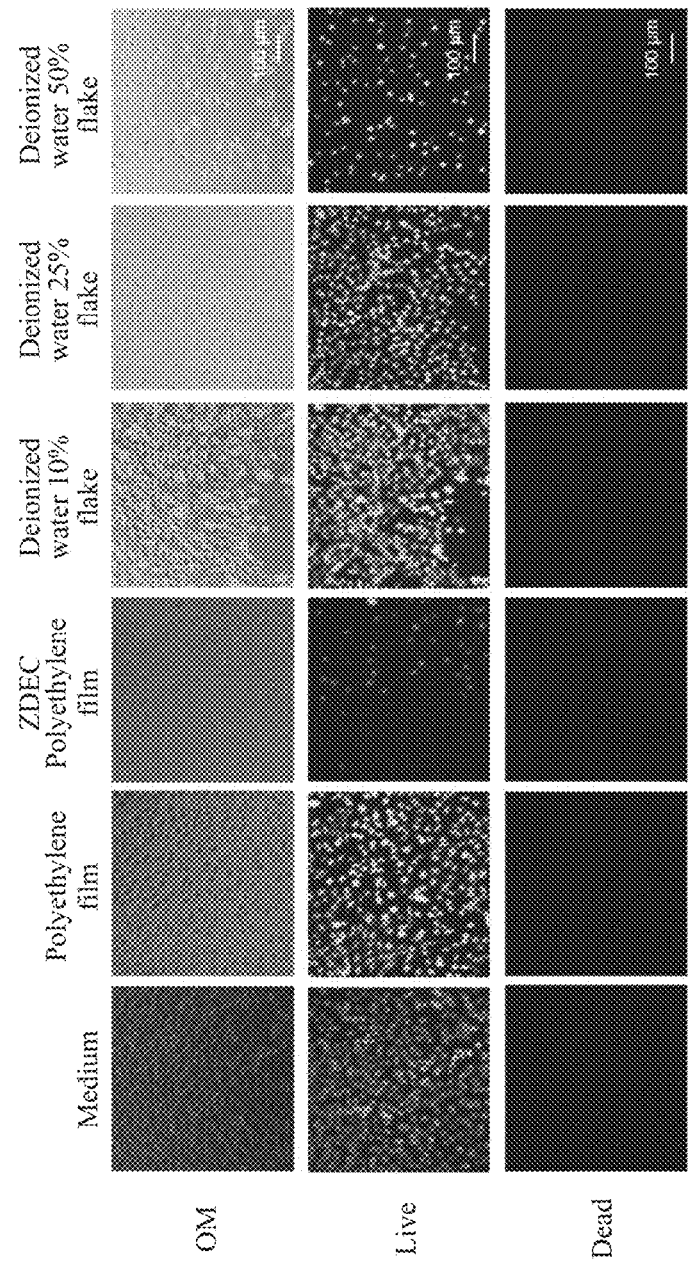
FIGS. 5A and 5B include images for explaining cell culture related to a channel layer constituting a transient sensor for each medium according to an embodiment of the present invention medium.
Figure 5B:
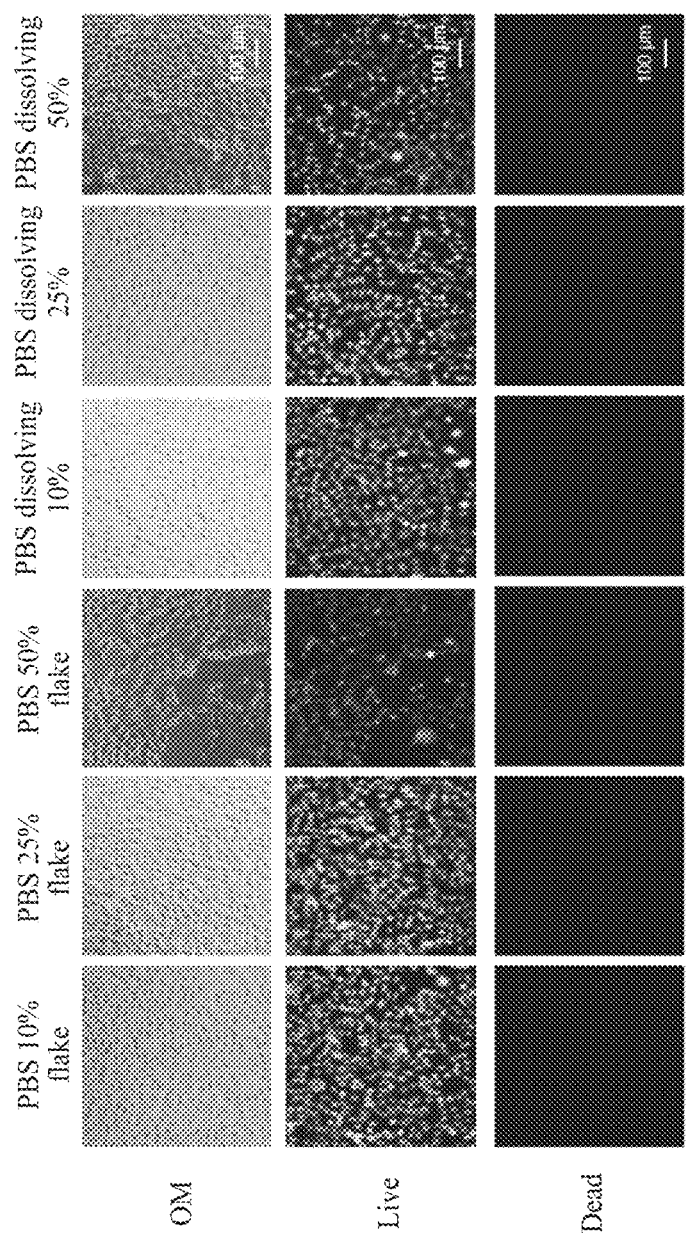
Figure 6A:
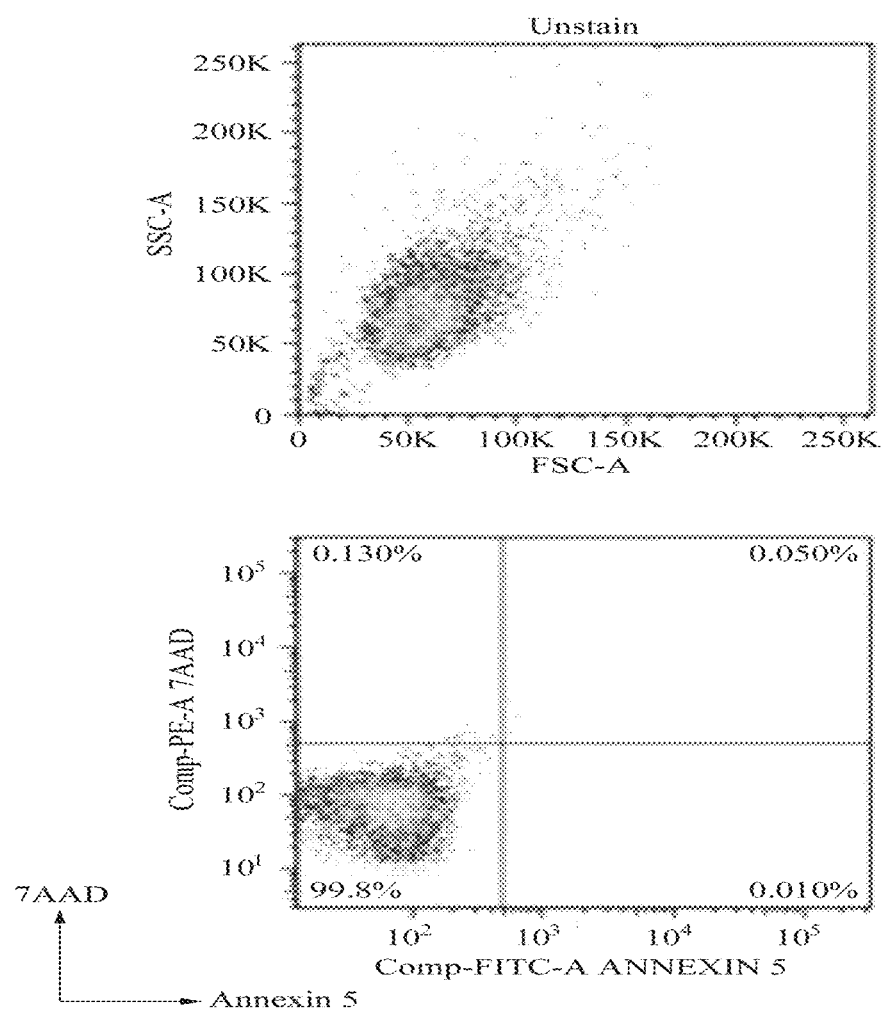
Figure 6B:
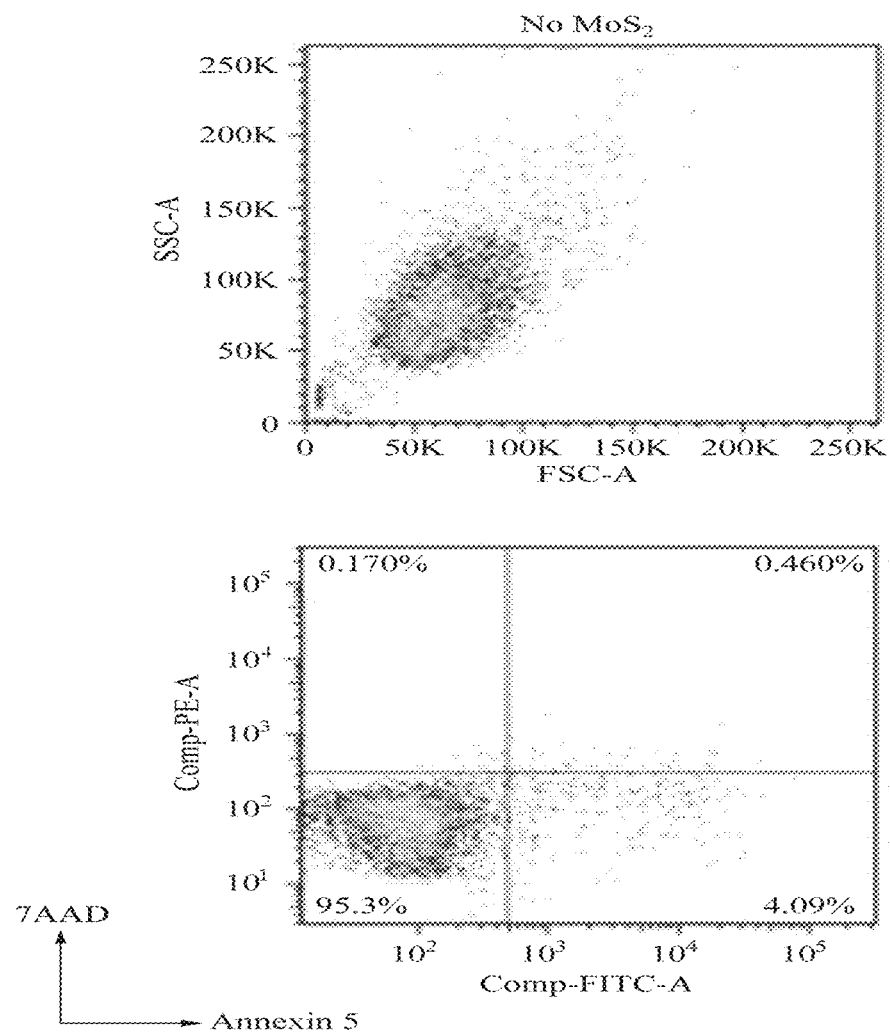
Figure 6C:
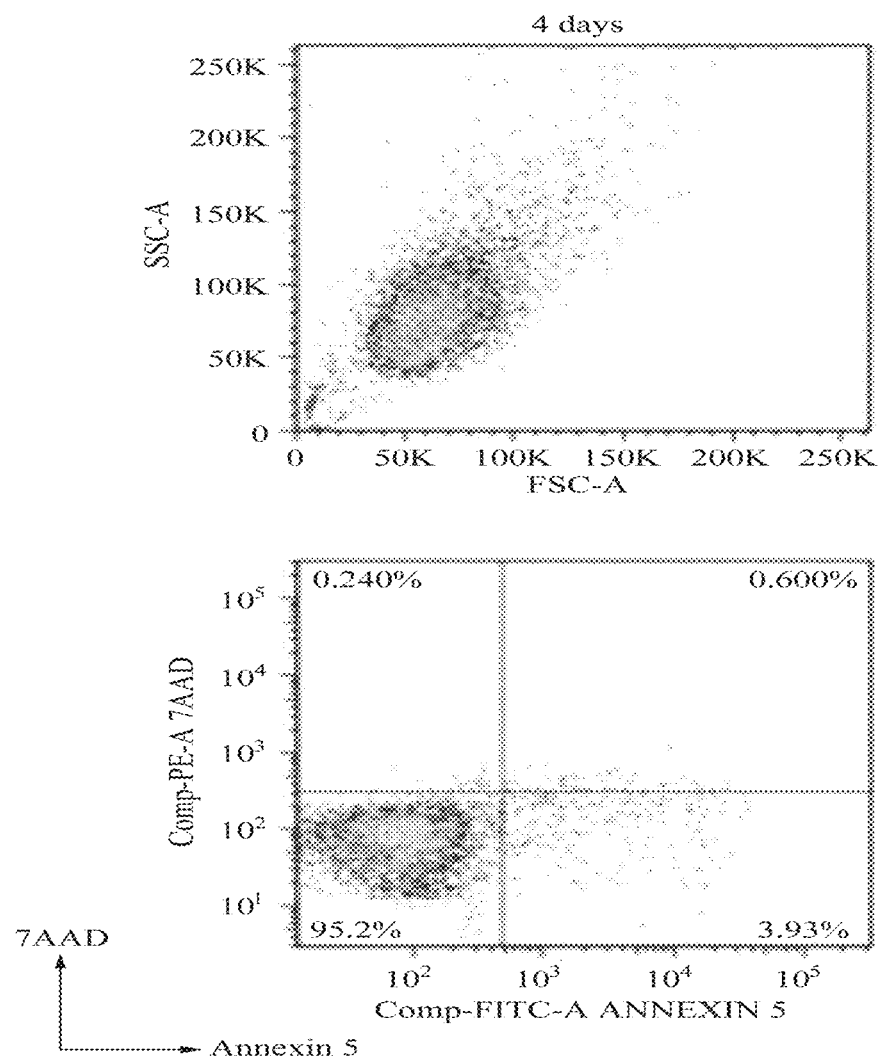
Figure 6E:
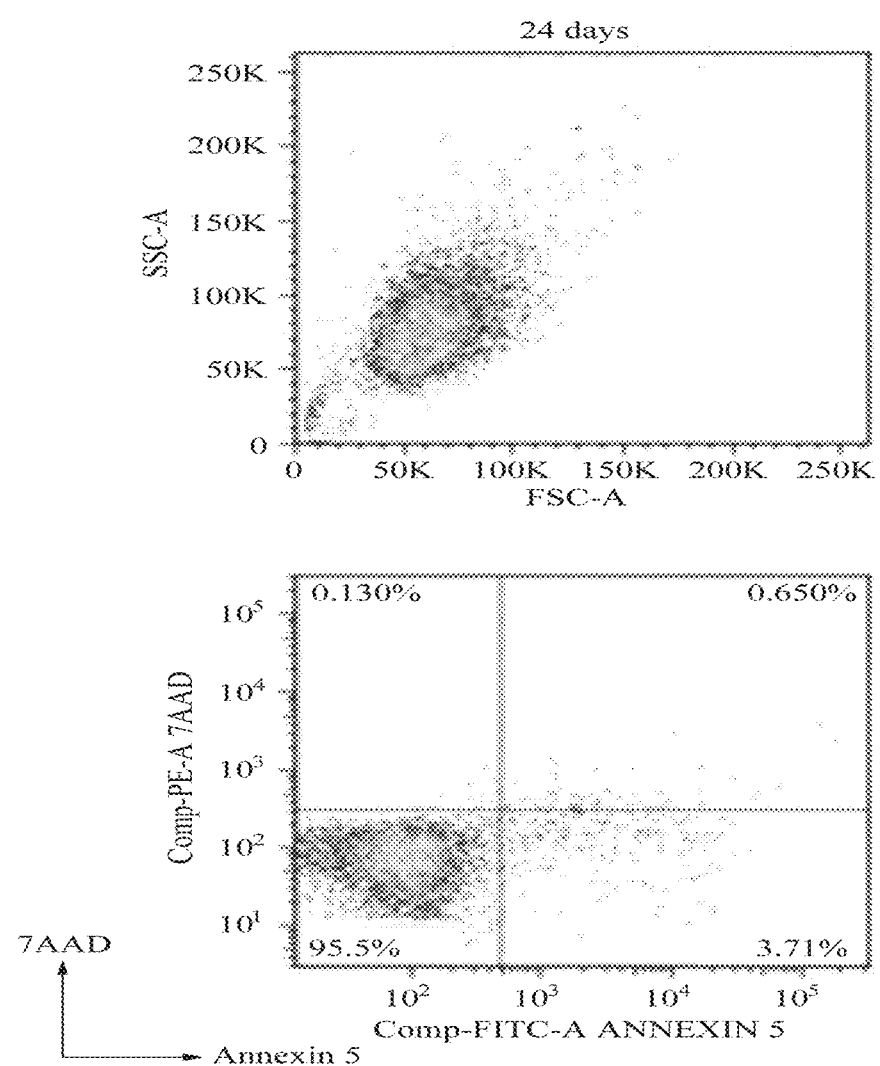

FIGS. 5A and 5B include images for explaining cell culture related to a channel layer constituting a transient sensor for each medium according to an embodiment of the present invention.

FIG. 5A includes images showing cell survival rate. Fluorescently labeled cells cultured for 4, 12, and 24 days in vitro, respectively, were incubated in a channel layer formed as a single layer using molybdenum disulfide supplied with medium or deionized water, or were incubated in a channel layer formed of a polyethylene film or a ZDEC polyethylene film supplied with the medium. After 24 days of incubation, cell survival rate under each condition was determined based on flakes.

FIG. 5B shows cell survival rate depending on the ratio of flakes in culture medium and changes in the dissolution rate. According to the results, the ratio of immune cells found in the peripheral blood may be determined based on the number of fluorescent substances.

Therefore, according to the method of manufacturing a transient sensor using molybdenum disulfide, biocompatibility of the transient sensor may be determined based on the ratio of immune cells present in the peripheral blood.

FIGS. 6A to 6E include graphs for explaining apoptosis related to a channel layer constituting a transient sensor according to an embodiment of the present invention.

Specifically, FIGS. 6A to 6E show the degree of apoptosis when the channel layer constituting the transient sensor is inserted into living matter.

Referring to FIGS. 6A to 6E, when a single layer formed of molybdenum disulfide using deposition is inserted into living matter, the degree of apoptosis may be analyzed over time based on the ratio between annexin and 7-aminoactinomycin (7-AAD).

Figure 7A:
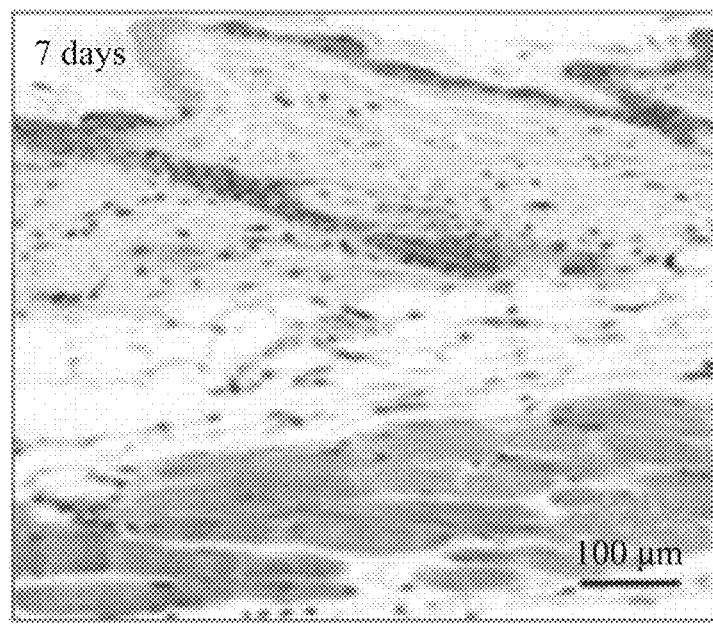
FIGS. 7A to 7C include images for explaining a cytotoxicity test using a transient sensor according to an embodiment of the present invention.
Figure 7B:
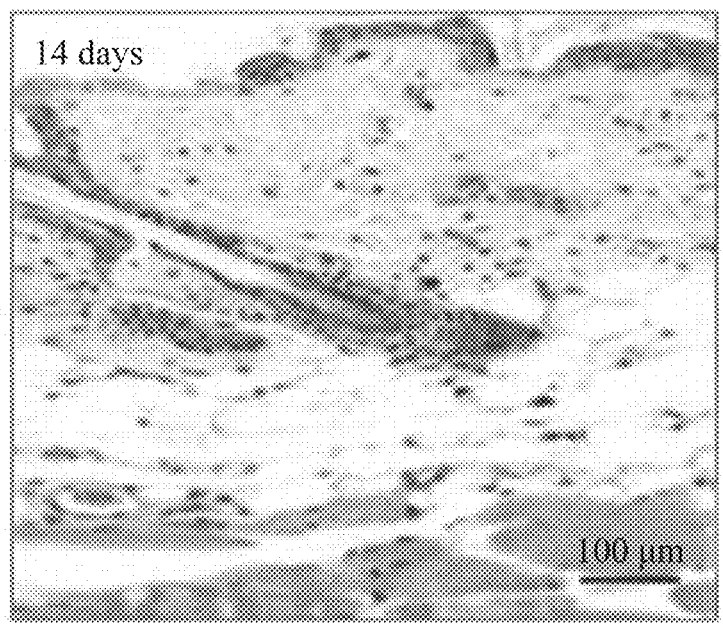
Figure 7C:
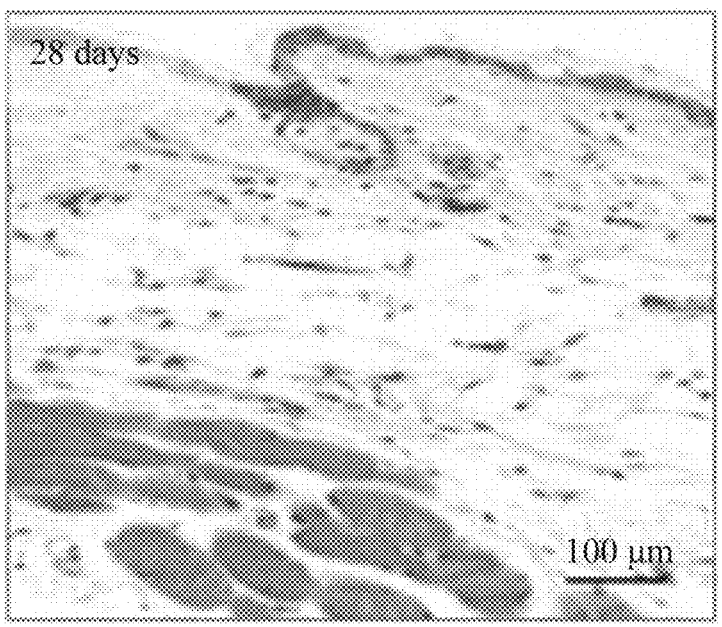

FIGS. 7A to 7C include images for explaining a cytotoxicity test using a transient sensor according to an embodiment of the present invention.

Specifically, FIGS. 7A to 7C show cellular changes in the subcutaneous layer over time.

FIG. 7A shows cell morphology in the subcutaneous layer after 7 days, FIG. 7B shows cell morphology in the subcutaneous layer after 14 days, and FIG. 7C shows cell morphology in the subcutaneous layer after 28 days.

To analyze cytotoxicity by insertion of the transient sensor, a sample sensor having a size of about 3 mm×10 mm is inserted into the muscle tissues of a rat and then cytotoxicity is analyzed.

Therefore, according to the present invention, a transient sensor that has excellent chemical stability and that can be manufactured to have a very thin thickness may be manufactured. According to the present invention, due to the chemical stability of the transient sensor, the transient sensor may not be easily transformed into other substances, and thus in vivo stability thereof may also be excellent. In addition, due to the thin thickness of the transient sensor, the dissolving time of the transient sensor in vivo may be remarkably reduced.

Figure 8A:
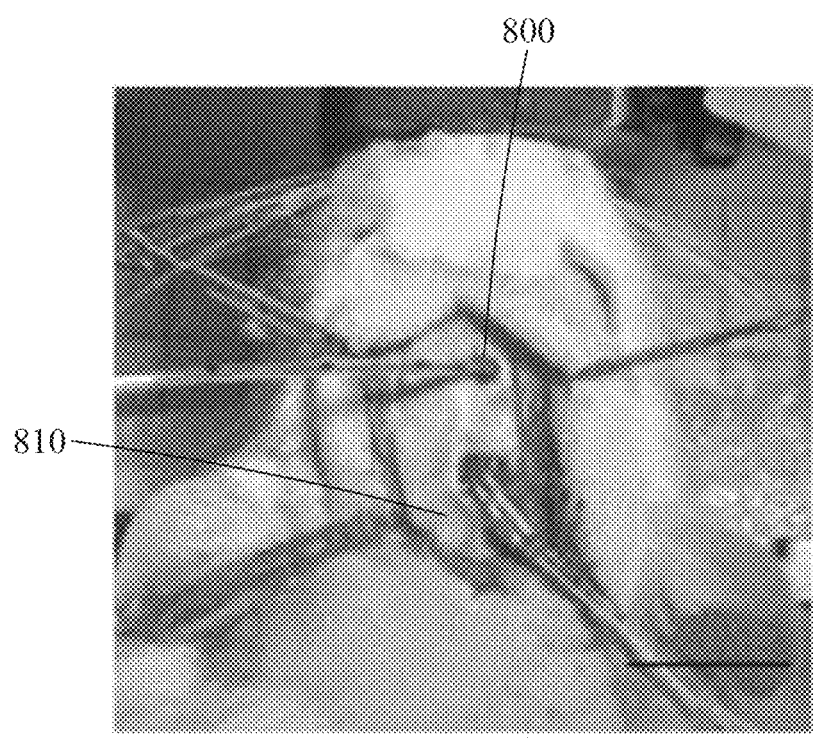
FIGS. 8A to 8C include images and a graph for comparing a transient sensor according to an embodiment of the present invention with a conventional biosensor.
Figure 8B:
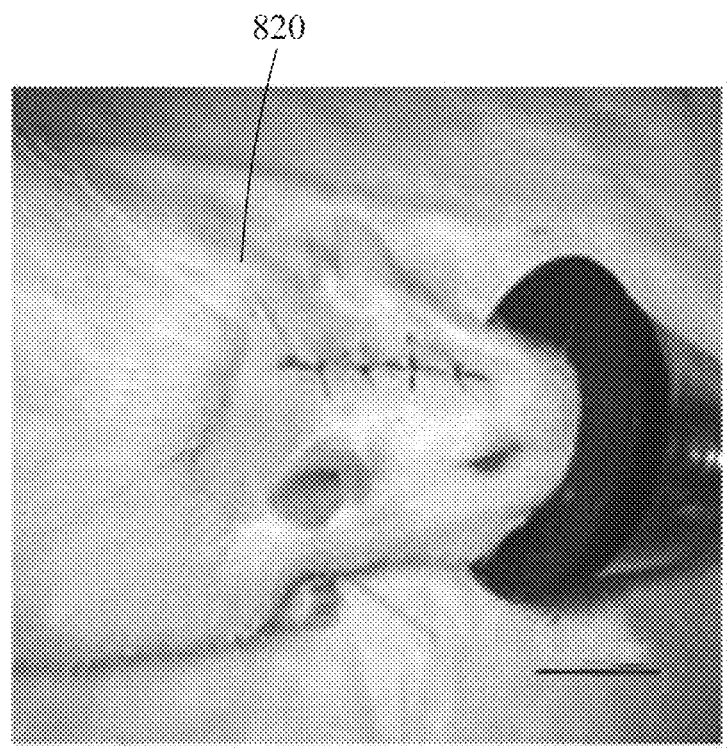
Figure 8C:
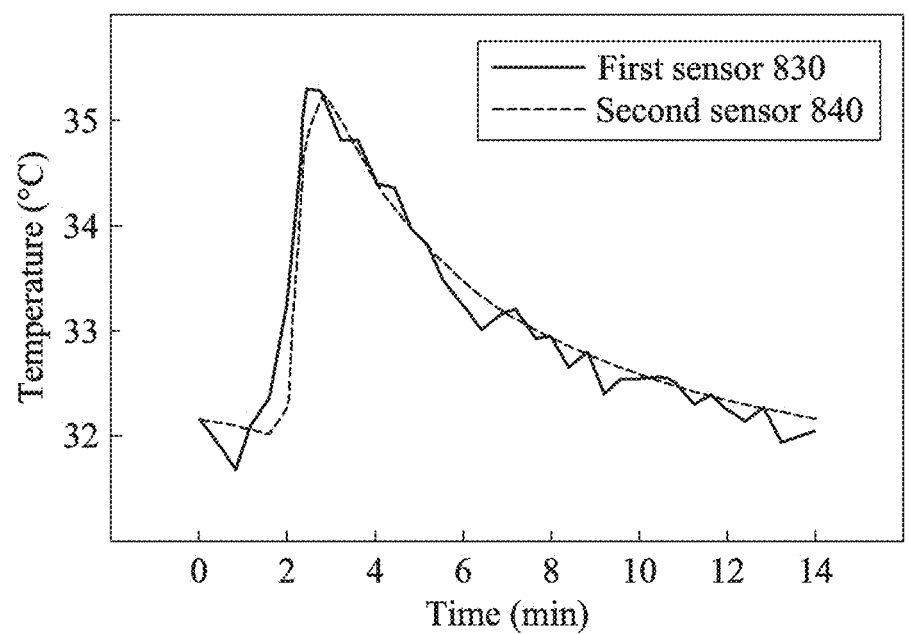

FIGS. 8A to 8C include images and a graph for comparing a transient sensor according to an embodiment of the present invention with a conventional biosensor.

FIGS. 8A and 8B include images showing a procedure for inserting a transient sensor into a laboratory mouse. Specifically, after the mouse head is excised, first and second sensors 800 and 810 are inserted, and then measurement cables are connected to the sensors.

Referring to FIG. 8A, the first and second sensors 800 and 810 are implanted in the head of a laboratory mouse. In this case, the first sensor 800 may be a general biosensor, and the second sensor 810 may be the transient sensor of the present invention.

Referring to FIG. 8B, after the excised portion of the laboratory mouse is sealed, data cables 820 are connected to the first and second sensors 800 and 810. In this embodiment, data is collected from the first and second sensors 800 and 810 using a wire such as a data cable, but the data may be collected wirelessly.

FIG. 8C is a graph showing temperature information collected from a laboratory mouse through first and second sensors 830 and 840.

In the graph, the horizontal axis corresponds to time, and the vertical axis corresponds to temperature. According to the graph, the first and second sensors collect similar data.

That is, the transient sensor according to an embodiment of the present invention has the same data collection capabilities as a commonly used biosensor.

Figure 9:
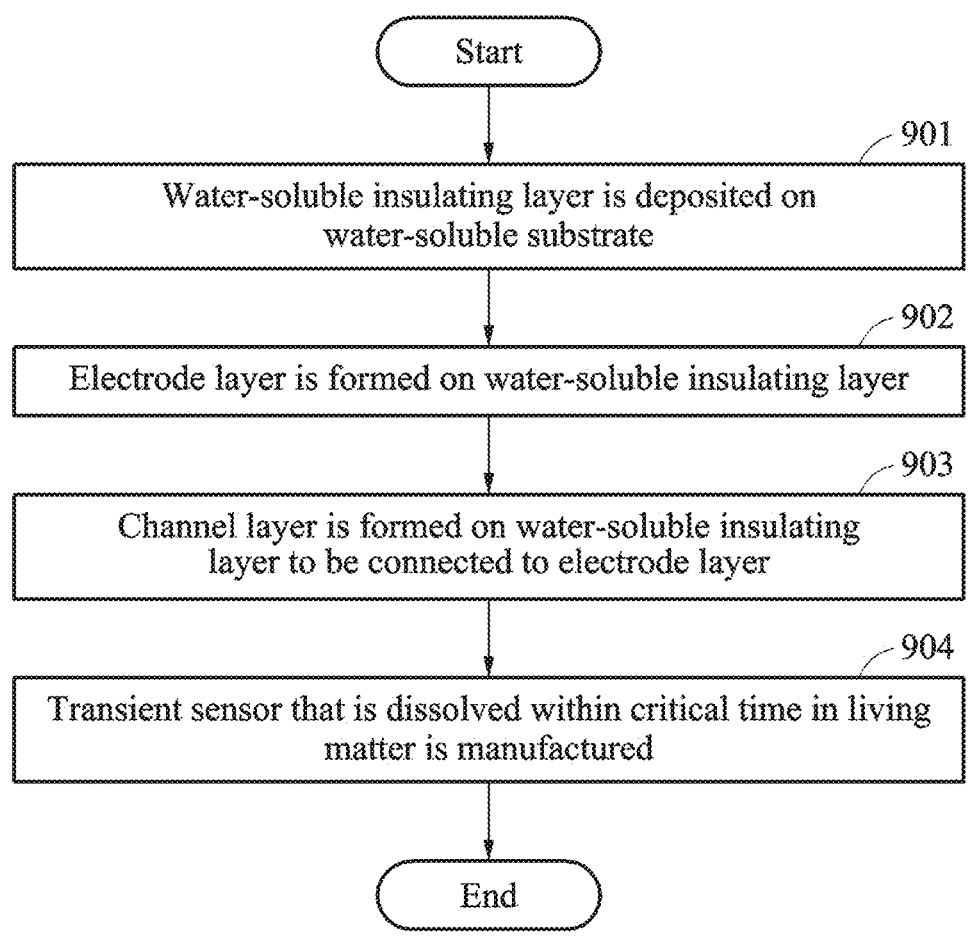
FIG. 9 is a flowchart for explaining a method of manufacturing a transient sensor according to an embodiment of the present invention.

FIG. 9 is a flowchart for explaining a method of manufacturing a transient sensor according to an embodiment of the present invention.

Referring to FIG. 9, in step 901, a water-soluble insulating layer may be deposited on a water-soluble substrate.

That is, according to the method of manufacturing a transient sensor, a water-soluble insulating layer may be formed on a water-soluble substrate formed of any one of poly(lactic-co-glycolic acid) (PLGA) and polyvinyl alcohol (PVA) by depositing any one of silicon oxide ($SiO_2$), silicon nitride ($Si_3N_4$), hafnium oxide ($HfO_2$), and magnesium oxide (MgO) based on atmospheric pressure chemical vapor deposition (APCVD).

In step 902, an electrode layer may be formed on a water-soluble insulating layer.

That is, according to the method of manufacturing a transient sensor, the electrode layer may be formed by depositing any one of molybdenum and magnesium (Mg) on the water-soluble insulating layer using chemical vapor deposition.

In step 903, a channel layer may be formed on the water-soluble insulating layer to be connected to the electrode layer.

That is, according to the method of manufacturing a transient sensor, the channel layer may be formed on the water-soluble insulating layer using molybdenum disulfide.

In step 904, the transient sensor that is dissolved within a critical time in living matter may be manufactured.

That is, according to the method of manufacturing a transient sensor, the transient sensor may include the water-soluble substrate, the water-soluble insulating layer, the electrode layer, and the channel layer. When the transient sensor is inserted into living matter, the transient sensor may be dissolved within a critical time in the living matter.

In addition, the method of manufacturing a transient sensor may further include a step of measuring at least one of bioabsorbability, pressure, temperature, strain, and acceleration of living matter through the channel layer.

In addition, the method of manufacturing a transient sensor may further include a step of determining biocompatibility of the channel layer based on the ratio of immune cells present in the peripheral blood of living matter into which the transient sensor is inserted and based on change in weight of the living matter.

Therefore, the present invention may provide a method of manufacturing a transient sensor. According to the present invention, the method may improve economic efficiency in lab-on-a-chip and wearable electronic device fields and may contribute to leading research on bio-nanomaterials In the above-described specific embodiments, elements included in the invention have been expressed singular or plural in accordance with the specific embodiments shown.

However, for ease of explanation, the singular or plural expressions are appropriately selected in accordance with the situation. The above-described embodiments are not limited to the singular or plural representations. Components expressed in plural forms may be in singular form, and vice versa.

In addition, although the present invention has been described with reference to specific embodiments, various modifications are possible without departing from the scope of the technical idea contained in the various embodiments.

Therefore, it should be understood that there is no intent to limit the invention to the embodiments disclosed, rather, the invention is to cover all modifications, equivalents, and alternatives falling within the spirit and scope of the invention as defined by the claims.

DESCRIPTION OF SYMBOLS

100: WATER-SOLUBLE SUBSTRATE
110: WATER-SOLUBLE INSULATING LAYER
120: ELECTRODE LAYER
130: CHANNEL LAYER

What is claimed is:

1. A transient sensor using molybdenum disulfide, comprising:
   a water-soluble substrate;
   a first water-soluble insulating layer deposited on the water-soluble substrate by depositing an oxide using atmospheric pressure chemical vapor deposition (APCVD);
   an electrode layer formed of any one of molybdenum (Mo) and magnesium (Mg) and formed on the first water-soluble insulating layer;
   a channel layer comprising molybdenum disulfide ($MoS_2$), tungsten sulfide ($WS_2$), selenium molybdenum ($MoSe_2$), tungsten diselenide ($WSe_2$), or molybdenum ditelluride ($MoTe_2$) in particle form formed on the first water-soluble insulating layer to be connected to the electrode layer; and
   a second water-soluble insulating layer additionally laminated on the electrode layer and the channel layer,
   wherein, when the transient sensor is inserted into living matter, the transient sensor is dissolved within a critical time in the living matter,
   wherein a top layer of the transient sensor is encapsulated using a polymer material,
   wherein the channel layer measures at least one of bioabsorbability, pressure, temperature, strain, and acceleration of the living matter,
   wherein the channel layer has a polycrystalline structure and is deposited as a single-layer film on the first water-soluble insulating layer, wherein biocompatibility of the channel layer is determined based on a ratio of immune cells present in peripheral blood contained in the living matter into which the transient sensor is inserted and weight change of the living matter into which the transient sensor is inserted,
   wherein the channel layer is deposited as a single layer on the first water-soluble insulating layer using metal-organic chemical vapor deposition (MOCVD) or is deposited by performing electron beam deposition on the electrode layer, and a channel is deposited in a square wave form in the channel layer, wherein the channel is connected to the electrode layer,
   wherein the critical time is determined based on a particle size of the channel layer deposited using the metal-organic chemical vapor deposition (MOCVD),
   wherein the electrode layer has a first electrode having a plurality of first finger patterns, and a second electrode having a plurality of second finger patterns interdigitated with the plurality of first finger patterns,
   wherein the channel layer, the first electrode and the second electrode each has a sidewall, and
   wherein the channel layer comprises a channel pattern inlaid between the first finger patterns and the second finger patterns, and sidewalls of the channel pattern contact sidewalls of the first finger patterns and the second finger patterns.

2. The transient sensor according to claim 1, wherein the water-soluble substrate is formed of any one of poly(lactic-co-glycolic acid) (PLGA) and polyvinyl alcohol (PVA).

3. The transient sensor according to claim 1, wherein the first water-soluble insulating layer is formed of any one of an oxide layer and a water-soluble polymer complex by depositing any one of silicon oxide ($SiO_2$), silicon nitride ($Si_3N_4$), hafnium oxide ($HfO_2$), and magnesium oxide (MgO) and is deposited on the water-soluble substrate using atmospheric pressure chemical vapor deposition (APCVD).

4. The transient sensor according to claim 1, wherein at least one of the water-soluble substrate, the first water-soluble insulating layer, the electrode layer, and the channel layer is dissolved in bodily fluid contained in the living matter.

* * * * *